United States Patent
Detwiler et al.

(10) Patent No.: US 6,482,310 B2
(45) Date of Patent: Nov. 19, 2002

(54) CURRENT CONTROL FOR A PUMPED AIR REFERENCE OXYGEN SENSOR

(75) Inventors: Eric J. Detwiler, Davison, MI (US); Richard C. Kuisell, Lapeer, MI (US); Joseph V. Bonadies, Clarkston, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/740,355

(22) Filed: Dec. 18, 2000

(65) Prior Publication Data

US 2002/0100698 A1 Aug. 1, 2002

(51) Int. Cl.[7] .............................................. G01N 27/41
(52) U.S. Cl. .................... 205/784.5; 123/685; 701/109; 701/113
(58) Field of Search ............................... 205/784, 784.5, 205/785; 204/424, 425, 426–429; 60/274, 276; 123/685, 688, 697; 701/109, 113

(56) References Cited

U.S. PATENT DOCUMENTS

| | | | |
|---|---|---|---|
| 4,272,329 A | 6/1981 | Hetrick et al. | |
| 4,570,479 A | 2/1986 | Sakurai et al. | |
| 4,839,018 A | 6/1989 | Yamada et al. | |
| 4,863,584 A | 9/1989 | Kojima et al. | |
| 5,509,267 A | * 4/1996 | Theis | 60/274 |
| 5,700,367 A | * 12/1997 | Yamada et al. | 204/408 |
| 5,815,828 A | * 9/1998 | Nankee et al. | 60/276 |
| 5,877,413 A | * 3/1999 | Hamburg et al. | 60/277 |
| 5,896,743 A | * 4/1999 | Griffin | 60/274 |

* cited by examiner

Primary Examiner—Robert J. Warden, Sr.
Assistant Examiner—Kaj K. Olsen
(74) Attorney, Agent, or Firm—Vincent A. Cichosz

(57) ABSTRACT

A method for applying and controlling current applied to an air reference oxygen sensor included in a vehicle exhaust system is disclosed. In an exemplary embodiment of the invention, the method includes measuring an output voltage across the oxygen sensor when the exhaust system is initially activated and applying a current through the oxygen sensor when the output voltage reaches a value determinative of light off of a catalyst within the exhaust system. The magnitude of the applied current corresponds to a predefined purge value.

10 Claims, 4 Drawing Sheets

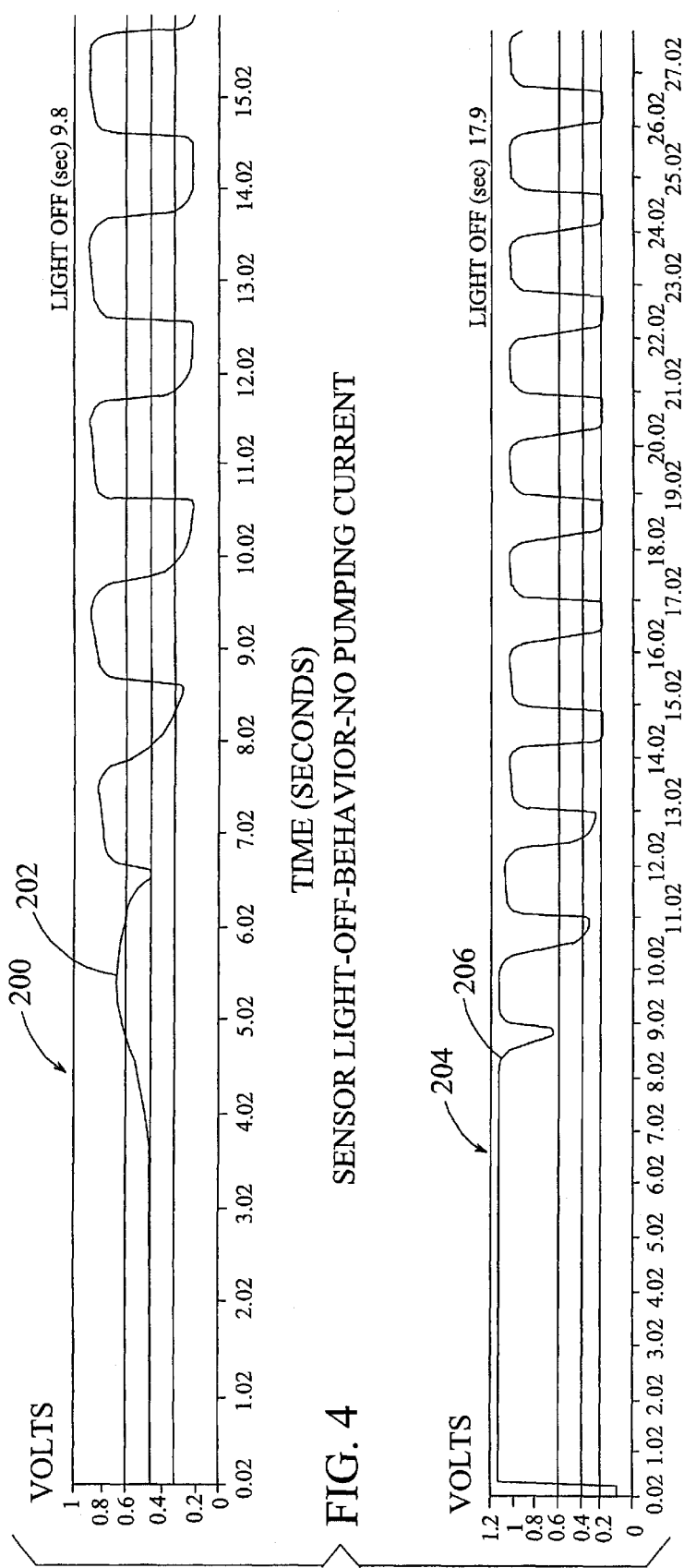

CURRENT CONTROL FOR A PUMPED AIR REFERENCE OXYGEN SENSOR

TECHNICAL FIELD

The present invention relates generally to oxygen sensors. More particularly, the present invention relates to a method for applying and controlling current to a pumped air reference oxygen sensor.

BACKGROUND OF THE INVENTION

Oxygen sensors are used in a variety of applications that require qualitative and quantitative analysis of gases. For example, oxygen sensors have been used for many years in automotive vehicles to sense the presence of oxygen in exhaust gases. More specifically, oxygen sensors may be used to sense when an exhaust gas content switches from rich to lean or lean to rich. In automotive applications, the direct relationship between oxygen concentration in the exhaust gas and the air-to-fuel ratios of the fuel mixture supplied to the engine allows the oxygen sensor to provide oxygen concentration measurements for determination of optimum combustion conditions, maximization of fuel economy, and the management of exhaust emissions.

A conventional stoichiometric oxygen sensor generally includes an ionically conductive solid electrolyte material, a porous electrode on the sensor's exterior exposed to the exhaust gases with a porous protective overcoat, and a porous electrode on the sensor's interior surface exposed to a known oxygen partial pressure. Sensors typically used in automotive applications use a yttria stabilized, zirconia based electrochemical galvanic cell with porous platinum electrodes, operating in potentiometric mode, to detect the relative amounts of oxygen present in an automobile engine's exhaust. When opposite surfaces of this galvanic cell are exposed to different oxygen partial pressures, an electromotive force is developed between the electrodes on the opposite surfaces of the zirconia wall, according to the Nernst equation:

$$E = \left(\frac{-RT}{4F}\right) \ln\left(\frac{P_{O_2}^{ref}}{P_{O_2}}\right)$$

where:
E=electromotive force
R=universal gas constant
F=Faraday constant
T=absolute temperature of the gas
$p_{O2}^{ref}$=oxygen partial pressure of the reference gas
$P_{O2}$=oxygen partial pressure of the exhaust gas Due to the large difference in oxygen partial pressures between fuel rich and fuel lean exhaust conditions, the electromotive force changes sharply at the stoichiometric point, giving rise to the characteristic switching behavior of these sensors. Consequently, these potentiometric oxygen sensors indicate qualitatively whether the engine is operating fuel rich or fuel lean, without quantifying the actual air to fuel ratio of the exhaust mixture. Increased demand for improved fuel economy and emissions control has necessitated the development of oxygen sensors capable of quantifying the exhaust oxygen partial pressure over a wide range of air fuel mixtures in both fuel-rich and fuel-lean conditions.

Conventional sensors use two types of air reference electrodes. The first type has a sizeable air chamber to provide oxygen from an ambient air supply to the reference electrode. However, to avoid contamination by the exhaust gas, the air chamber requires a hermetic seal sensor package, which is expensive and is problematic in field applications. The second type is a pumped-air reference electrode. It uses a pump circuit to pump oxygen from the exhaust gas to the reference electrode. As such, it does not require a sizeable air chamber connected to ambient air. Nor does it require a hermetic seal sensor package.

Pumped air reference oxygen sensors are advantageous over sealed oxygen sensors, as the latter are subject to air reference contamination. However, there are also some drawbacks associated with pumping current applied to pumped air reference oxygen sensors, such as the internal resistance of the sensor. During "key on" of the system, a DC offset voltage is introduced on the sensor output signal that, in turn, increases the system light-off time. In addition, pumped air reference sensors may also be susceptible to air reference contamination following engine shut down and during a subsequent start up.

It is therefore desirable to provide a method of controlling the pumping current applied to a pumped air reference oxygen sensor that addresses the aforementioned concerns.

SUMMARY OF THE INVENTION

The problems and disadvantages of the prior art are overcome and alleviated by a method for applying and controlling current applied to an air reference oxygen sensor included in a vehicle exhaust system. In an exemplary embodiment of the invention, the method includes measuring an output voltage across the oxygen sensor when the exhaust system is initially activated and applying a current through the oxygen sensor when the output voltage reaches a value determinative of light off of a catalyst within the exhaust system. The magnitude of the applied current corresponds to a predefined purge value.

In a preferred embodiment, the method also includes monitoring an exhaust temperature in the system and decreasing the magnitude of the current applied through the oxygen sensor from the predefined purge value if the exhaust temperature indicates that the exhaust system is operating at a first condition. Conversely, the magnitude of the current applied through the oxygen sensor is increased from the predefined purge value if the exhaust temperature indicates that the exhaust system is operating at a second condition.

BRIEF DESCRIPTION OF THE DRAWINGS

The present invention will now be described, by way of example only, with reference to the accompanying drawings which are meant to be exemplary, not limiting, and wherein like elements are numbered alike in several Figures, in which:

FIG. 4 is a pair of graphs illustrating a comparison between the output signals of an oxygen sensor with and without pumping current applied thereto.

DESCRIPTION OF THE PREFERRED EMBODIMENT

Figure 1:
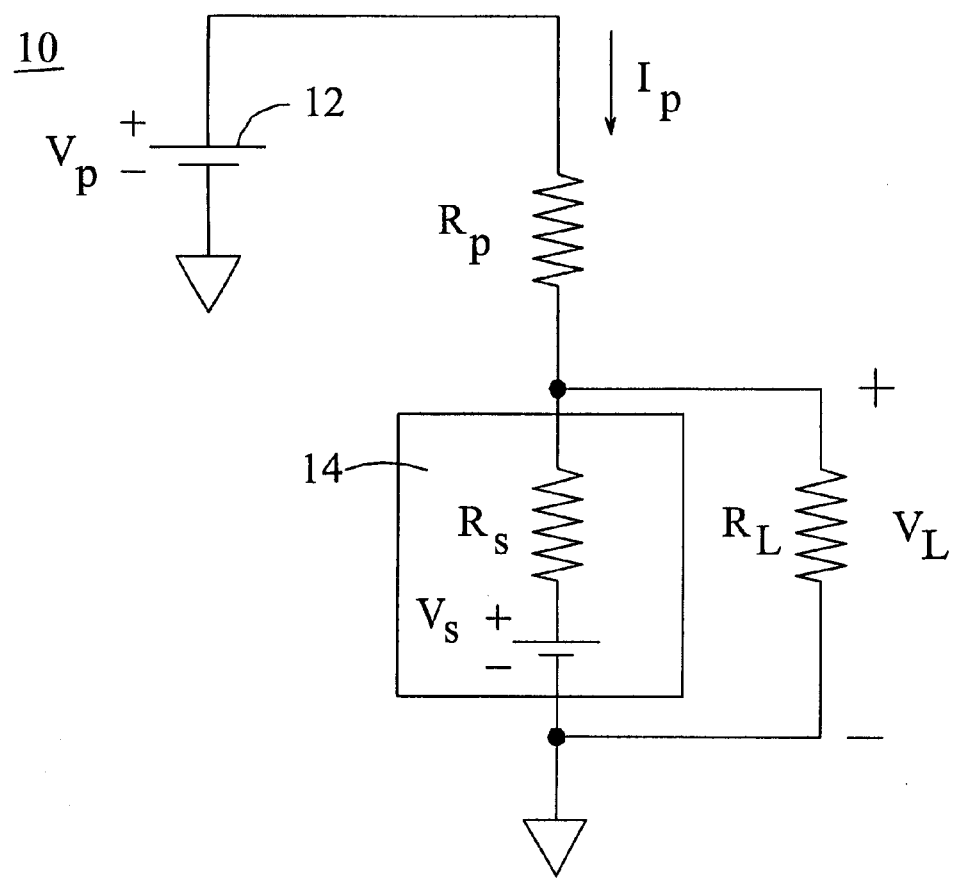
FIG. 1 is schematic diagram of a known system for applying pumping current to a pumped air reference oxygen system.

Referring initially to FIG. 1, there is illustrated a schematic diagram representing a known apparatus 10 for applying current to a pumped air reference oxygen sensor. An oxygen pumping voltage source 12, having a voltage designated by $V_P$, supplies pumping current to a zirconia based oxygen sensor 14. Typically, $V_P$ is approximately 5 volts. A resistor, $R_P$, limits the amount of current applied to oxygen sensor 14. Sensor 14 has an internal ohmic resistance, represented in FIG. 1 by $R_S$, and a voltage $V_S$ induced across the sensor electrodes (not shown). As described earlier, voltage $V_S$ is a result of the generation of an electromotive force due to the differential in partial pressures of oxygen, as sensed by the electrodes of sensor 14. The value of $V_S$ is approximately 0 volts during lean exhaust conditions and approximately 900 mV during rich exhaust conditions. Finally, $R_L$ represents the high impedance load of a monitoring device (not shown), such as a voltmeter, which measures the output voltage ($V_L$) of sensor 14.

The value of $R_S$ is temperature dependent and is greatest during lower temperatures, such as in a "key on" state where the exhaust system has just been activated. The resistance of $R_S$ is given by:

$$R_S = \rho_S^* (L/A); \quad (1)$$

where $\rho_S$ is the bulk resistivity of the zirconia;

L is the thickness of the zirconia; and

A is the area of the electrode-zirconia interface.

The temperature dependence of the zirconia resistivity is reflected in the following equation:

$$\rho_S = 10^{-5}(e^{1eV/kT})T; \quad (2)$$

where 1 eV is the activation energy of zirconia k is Boltzmann's constant; and

T is absolute temperature.

Referring once again to the schematic shown in FIG. 1, it can be seen that the larger the value of $R_S$ (as is typically the case during an initial "key on" event), the greater the value of the offset voltage seen at $V_L$. As the operating temperature of sensor 14 increases, the value of $R_S$ is gradually reduced until the value of $V_L$ approaches $V_S$. During this time, however, the application of the pumping current from $V_P$, applied immediately upon "key on" adds a DC offset voltage which increases the time in which the sensor 14 determines the "light off" of the system. The "light off" time of the system is generally defined as the point at which the catalyst in the system reaches fifty percent efficiency over a period of time (measured in seconds) during start-up of the system. In addition to increasing the time taken by the sensor 14 in determining light off time, the offset voltage could even damage the sensor 14 under certain conditions during low temperature operation.

The prior art system represented in FIG. 1 applies pumping current immediately upon key on, maintaining a continuous source of current until such time as the system is keyed off or shut down. Once the system is shut down, no more pumping current is applied and the reference chamber is subject to contamination.

Figure 2:
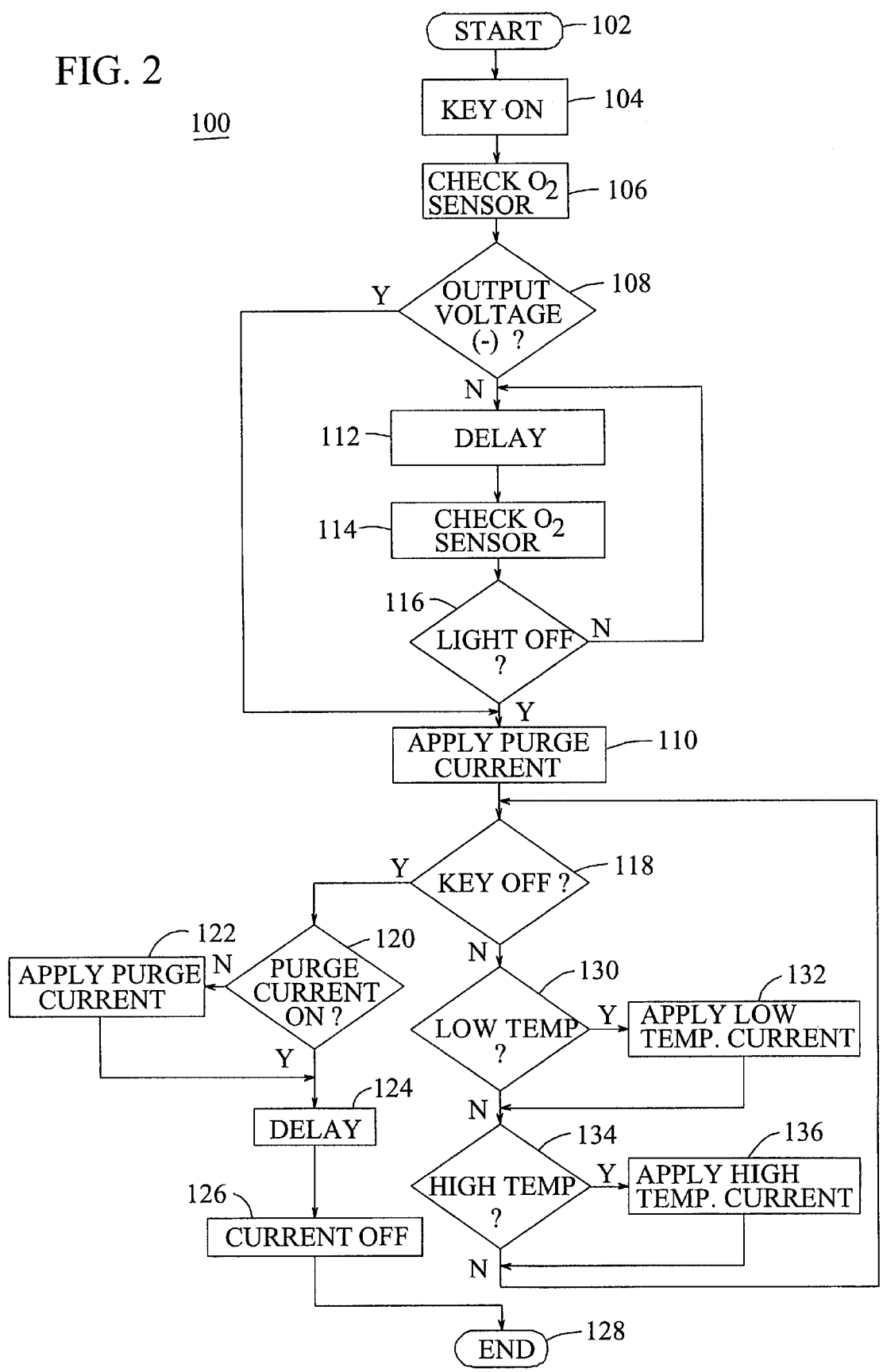
FIG. 2 is flow diagram illustrating a method of pumping current to a pumped air reference oxygen system, in accordance with an embodiment of the invention.

Referring now to FIG. 2, a method 100 of applying and controlling the pumping current to an oxygen sensor according to an embodiment of the invention is shown. Method 100 begins with a start block 102 and proceeds to block 104 where a system "key on" begins. The "key on" may represent the starting of an automotive combustion system. At block 106, the oxygen sensor is initially checked, and a determination is made at decision block 108 to determine whether or not a negative voltage exists across the sensor's electrodes. If so, the sensor is contaminated and method 100 proceeds immediately to block 110 where a predetermined value of "purge" pumping current is applied. If a negative voltage is not detected, a time delay is instituted at block 112 after "key on", whereby the pumping current is not yet applied. The output voltage of the sensor is then checked again at block 114. Another decision block 116 determines whether system light off has taken place. If not, then method 100 returns to block 112 for another delay and then the output voltage is once again checked at block 114 to see whether light off has taken place. Decision block 116 will continue to return to block to 112 until light off has finally taken place. At that point, method 100 then advances to block 110, where pumping current is applied. The pumping current is applied at a predetermined "purge" level. The "purge" level is typically about 7 µA, but may also be determined based upon system requirements.

Alternatively, method 100 may, if the sensor is not contaminated, proceed to block 112 and execute a predetermined delay (for example, 15 seconds) and then proceed to block 1 10 without performing the steps at blocks 114 and 116.

Unlike the prior art systems, method 100 will not remove the pumping current immediately upon system key off. In order to supply the reference chamber with oxygen to prevent contamination during shut off, the pumping current is applied for a period of time after key off. Thus, method 100 determines at decision block 118 whether system key off has taken place. If so, then decision block 120 will first determine if the appropriate level ("purge" value) of pumping current is actively being applied. If not, the pumping current will be adjusted at block 122 and method 100 proceeds to a delay at block 124. If the proper level of pumping current is being applied upon key off, then method proceeds directly to block 124. The delay at block 124 causes the pumping current to continue to be applied for a predetermined time period after key off. After the time period has expired, the current is finally removed at block 126, and method ends at end block 128.

In addition to applying a purge current following system light off (and for a period of time after key off), method 100 continues to monitor the output of oxygen sensor during system operation. The amount of pumping current applied during operation may subsequently be adjusted according to various engine conditions such as low exhaust temperature or high speed/high load/high temperature. Thus, returning to FIG. 2, if decision block 118 finds that the system has not been keyed off, then method 100 will proceed to decision block 130 to check whether a low exhaust temperature condition exists. If so, then the amount of pumping current is adjusted at block 132 to apply a predetermined "low temperature" value of current. Preferably, the "low temperature" value of applied current is less than that of the "purge" level of pumping current, since it is desirable to reduce the amount of DC offset voltage on the sensor output during low temperature operation. The value of low temperature current applied may be, for example, 5 µA.

Regardless of whether a low temperature condition exists, method 100 will also check to see whether a high speed/load/temperature condition exists at decision block 134. If so, then the amount of pumping current is adjusted at block 136 to apply a predetermined "high temperature" value of current. Preferably, the "high temperature" value of applied current is greater than that of the "purge" level of pumping current. For example, 10 µA of current may be used for high temperature operation. In this situation, more oxygen may be pumped into the reference chamber, while the resulting DC offset voltage will be minimal. After checking for both a low and a high temperature condition, method 100 will return to decision block 118 to determine whether key off has taken place. If not, the high and low temperature conditions will continue to be monitored and the level of pumping current adjusted as needed until key off occurs and method 100 comes to an end, as described above.

Figure 3:
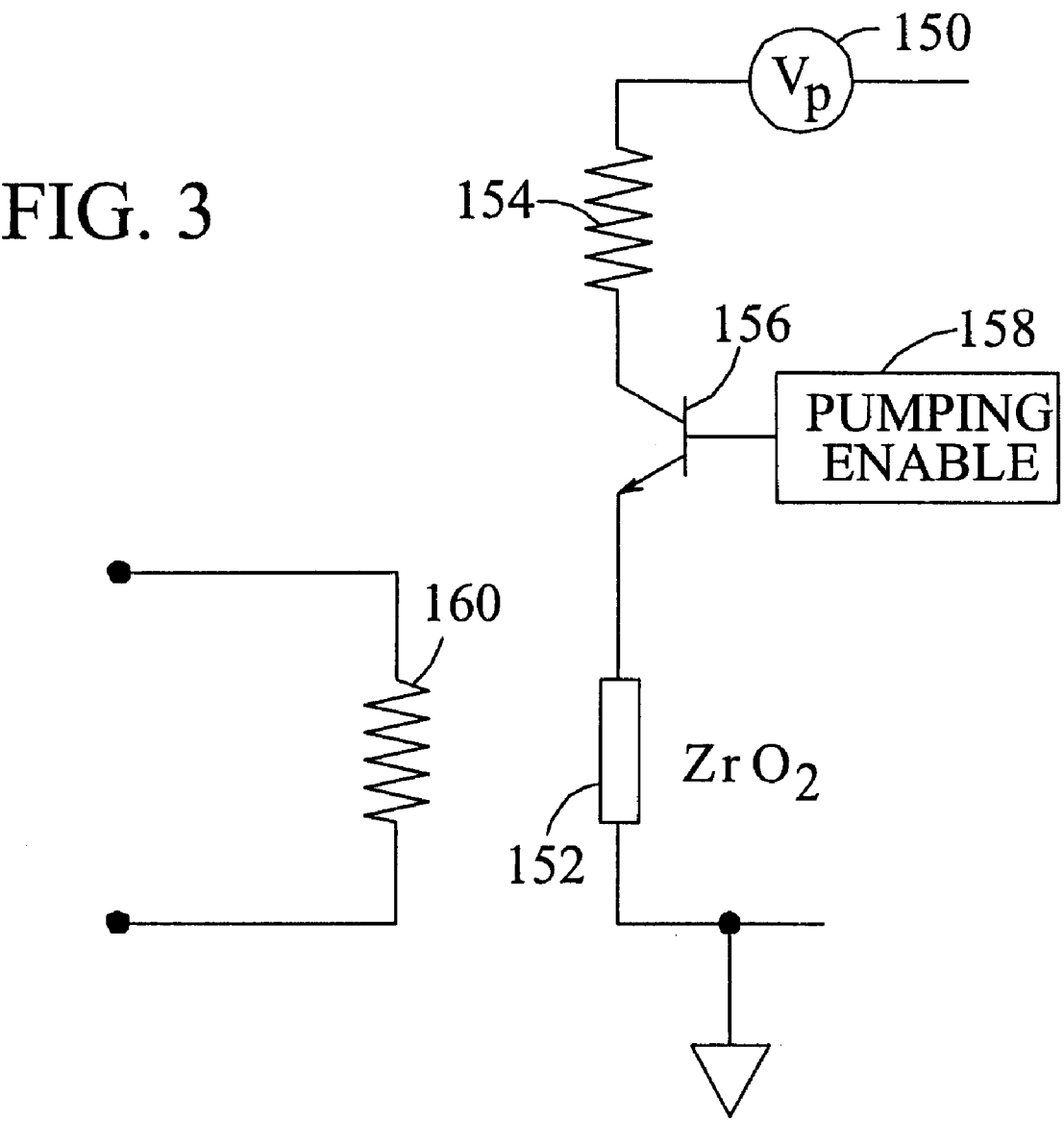
FIG. 3 is a schematic diagram of an embodiment of the method illustrated in FIG. 2.

FIG. 3 is a schematic diagram of one possible embodiment of applying pumping current in accordance with the method 100 illustrated by FIG. 2. A voltage source 150 provides a pumping current supply to an oxygen sensor 152 through resistor 154. A transistor 156 or other similar electronic switching device is used to selectively apply pumping current to sensor 152. The base of transistor 156 is controlled by a pumping enable signal 158 generated in accordance with method 100. A resistive heating element 160 may also be used to increase the operating temperature of sensor 152, thereby reducing the internal resistance therein. The pumping enable signal 158 may be used to control the current applied to sensor 152 by repetitive on/off, duty cycle switching. Alternatively, a regulated current supply (not shown) may be used in lieu of transistor 156.

Referring now to FIG. 4, there is shown a pair of graphs illustrating the output behavior of an oxygen sensor following a system key on test. In this particular application, the time in determining the system "light off" is reflected in the graphs as the amount of time taken for the voltage output signal to stabilize between 600 mV and 300 mV. In the first instance, graph 200 represents the sensor behavior without any pumping current applied thereto. As can be seen, there is no DC offset voltage added to the sensor output signal 202, since there is no internal voltage drop in the sensor associated with a pumping current. Further, the light off is determined at approximately 9.8 seconds. In the second instance, graph 204 depicts the sensor output voltage when a pumping current of 7 $\mu$A is applied to the sensor upon key on. This time, the applied pumping current results in a DC offset voltage on the sensor, as it has a relatively high internal resistance at key on. Eventually, the operating temperature is increased and the output signal 206 approaches the same pattern as signal 202. However, the light off determination time has now increased to approximately 17.9 seconds because of the additional time required for the offset voltage to decline down to a negligible level.

Because the disclosed embodiments of the invention provide for a delay in the application of pumping current upon key on, it is seen that the light off determination time can be reduced by not applying current to the sensor until light off has been achieved. Thus, the above discussed and other drawbacks and deficiencies of the prior art are overcome or alleviated by the present embodiments of the method for applying and controlling current to a pumped air reference oxygen sensor.

The disclosed invention may be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or as data signal transmitted whether a modulated carrier wave or not, over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for applying and controlling current to an air reference oxygen sensor, the oxygen sensor included in a vehicle exhaust system, the method comprising:

measuring an output voltage across the oxygen sensor when the exhaust system is initially activated; and applying a current through the oxygen sensor when said output voltage reaches a value determinative of light off of a catalyst within the exhaust system, the magnitude of said current corresponding to a predefined purge value.

2. The method of claim 1, further comprising applying said current through the oxygen sensor for a predetermined time period after said exhaust system has been deactivated.

3. The method of claim 2, further comprising applying said current through the oxygen sensor at said purge value for a predetermined time period after said exhaust system has been deactivated.

4. The method of claim 1, further comprising:

determining whether said output voltage across the oxygen sensor is negative when the exhaust system is initially activated; and if said output voltage across the oxygen sensor is not negative when the exhaust system is initially activated, then applying said current through the oxygen sensor when said output voltage reaches said value determinative of light off;

otherwise, if said output voltage across the oxygen sensor is negative when the exhaust system is initially activated, then immediately applying said current through the oxygen sensor;

said magnitude of said current corresponding to said predefined purge value.

5. The method of claim 1, further comprising:

monitoring an exhaust temperature in the system;

decreasing said magnitude of said current applied through the oxygen sensor from said predefined purge value if said exhaust temperature indicates that the exhaust system is operating at a first condition; and increasing said magnitude of said current applied through the oxygen sensor said predefined purge value if said exhaust temperature indicates that the exhaust system is operating at a second condition.

6. A storage medium encoded with a machine readable computer program code for applying and controlling current to an air reference oxygen sensor, the oxygen sensor included in a vehicle exhaust system, the storage medium including instructions for causing a computer to implement a method, the method comprising:

measuring an output voltage across the oxygen sensor when the exhaust system is initially activated; and applying a current through the oxygen sensor when said output voltage reaches a value determinative of light off of a catalyst within the exhaust system, the magnitude of said current corresponding to a predefined purge value.

7. The storage medium of claim 6, wherein said method further comprises applying said current through the oxygen sensor for a predetermined time period after said exhaust system has been deactivated.

8. The storage medium of claim 7, wherein said method further comprises applying said current through the oxygen sensor at said purge value for a predetermined time period after said exhaust system has been deactivated.

9. The storage medium of claim 6, wherein said method further comprises:

determining whether said output voltage across the oxygen sensor is negative when the exhaust system is initially activated; and if said output voltage across the oxygen sensor is not negative when the exhaust system is initially activated, then applying said current through the oxygen sensor when said output voltage reaches said value determinative of light off;

otherwise, if said output voltage across the oxygen sensor is negative when the exhaust system is initially activated, then immediately applying said current through the oxygen sensor;

said magnitude of said current corresponding to said predefined purge value.

10. The storage medium of claim 6, wherein said method further comprises:

monitoring an exhaust temperature in the system;

decreasing said magnitude of said current applied through the oxygen sensor from said predefined purge value if said exhaust temperature indicates that the exhaust system is operating at a first condition; and increasing said magnitude of said current applied through the oxygen sensor from said predefined purge value if said exhaust temperature indicates that the exhaust system is operating at a second condition.

* * * * *